United States Patent
Yang

(10) Patent No.: US 11,912,752 B2
(45) Date of Patent: Feb. 27, 2024

(54) PTH MIMETIC PEPTIDE BASED ON PROTEIN DOMAIN RECONSTRUCTION AND APPLICATION THEREOF

(71) Applicant: Dehong Yang, Guangdong (CN)

(72) Inventor: Dehong Yang, Guangdong (CN)

( * ) Notice: Subject to any disclaimer, the term of this patent is extended or adjusted under 35 U.S.C. 154(b) by 288 days.

(21) Appl. No.: 17/243,589

(22) Filed: Apr. 29, 2021

(65) Prior Publication Data

US 2021/0253663 A1   Aug. 19, 2021

Related U.S. Application Data

(63) Continuation-in-part of application No. PCT/CN2018/114335, filed on Nov. 7, 2018.

(30) Foreign Application Priority Data

Oct. 31, 2018 (CN) .......................... 201811284147.2

(51) Int. Cl.
*C07K 14/635* (2006.01)
*A61P 19/10* (2006.01)
*A61K 38/00* (2006.01)

(52) U.S. Cl.
CPC ............ *C07K 14/635* (2013.01); *A61P 19/10* (2018.01); *A61K 38/00* (2013.01)

(58) Field of Classification Search
CPC ........ C07K 14/635; A61P 19/10; A61P 19/08; A61K 38/00
See application file for complete search history.

(56) References Cited

FOREIGN PATENT DOCUMENTS

| CN | 1311256 | 9/2001 |
| CN | 106366176 | 2/2017 |
| CN | 108276487 | 7/2018 |

OTHER PUBLICATIONS

Guojun Tong et al., "Parathyroid Hormone Activates Phospholipase C (PLC)-Independent Protein Kinase C Signaling Pathway via Protein Kinase A (PKA)-Dependent Mechanism: A New Defined Signaling Route Would Induce Alternative Consideration to Previous Conceptions," Med Sci Monit., vol. 23, Apr. 20, 2017, pp. 1896-1906.

Wei Li et al., "Phospholipase C signaling activated by parathyroid hormone mediates the rapid osteoclastogenesis in the fracture healing of orchiectomized mice," BMC Musculoskeletal Disorders, vol. 19, Article No. 311, Aug. 29, 2018, pp. 1-12.

Song Hao, "The design of PLC-independent PKC signaling pathway selective PTH peptide and its effects on bone metabolism", Thesis of Master Degree, Southern Medical University, Mar. 2015, pp. 1-76.

*Primary Examiner* — Julie Ha
*Assistant Examiner* — Erinne R Dabkowski
(74) *Attorney, Agent, or Firm* — JCIP GLOBAL INC.

(57) ABSTRACT

A novel PTH(1-34) mimetic peptide based on protein domain reconstruction. The mimetic peptide contains peptide fragment repeats at 29th-34th positions. The amino acid at the 34th position and the last amino acid of the peptide fragment repeats at the 29th-34th positions are changed from phenylalanine (Phe, F) into tyrosine (Tyr, Y), so that MY-3 peptide is formed. Preclinical experiments show that the MY-3 mimetic peptide promotes osteoblast differentiation and has a very good effect in treating osteoporosis and promoting bone growth. The anti-osteoporosis effect of the MY-3 mimetic peptide is better than that of the PTH (1-34) (The product name on the market is Forsteo or Parathyroid), so that the MY-3 mimetic peptide has a significant clinical application prospect.

2 Claims, 5 Drawing Sheets

Specification includes a Sequence Listing.

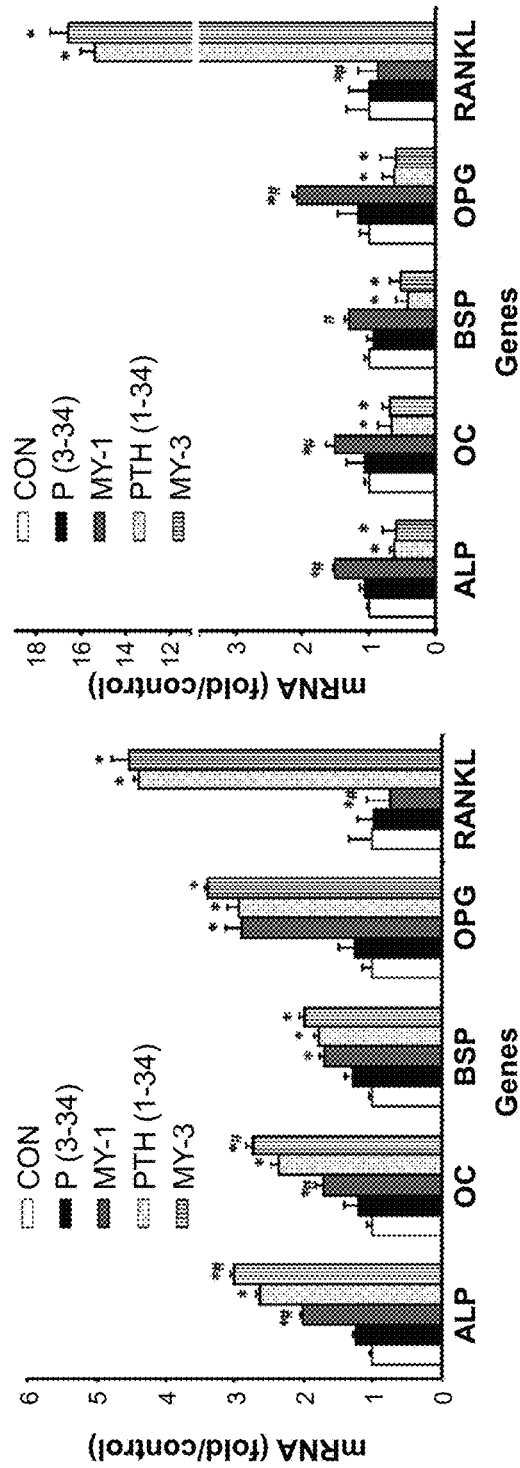
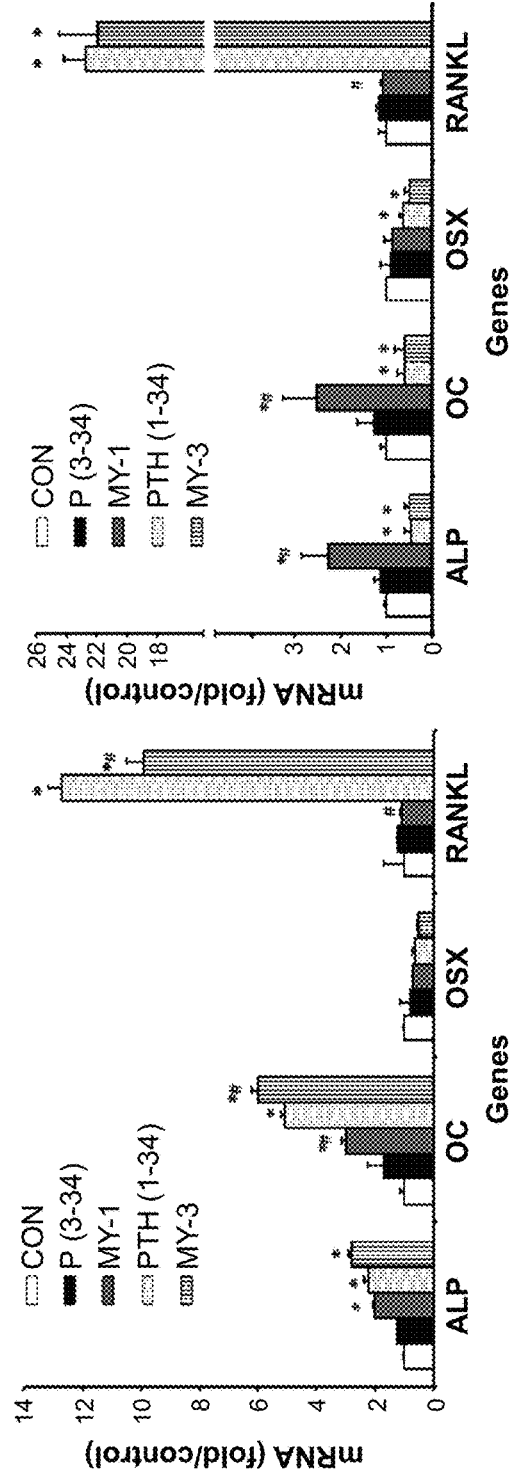
FIG. 3A
FIG. 3B
FIG. 3C
FIG. 3D

Table 1 Effects of PTH mimetic peptides in anti-bone loss through micro-CT observation (2 W, n=8)

|  | sham | OVX | | | | |
|---|---|---|---|---|---|---|
|  |  | Vehicle | PTH(3-34) | MY-1 | PTH(1-34) | MY-3 |
| BV/TV | 0.127±0.006* | 0.093±0.006 | 0.094±0.009 | 0.113±0.012* | 0.118±0.010* | 0.120±0.009* |
| BMD | 93.387±25.392 | 66.507±32.017 | 63.236±30.556 | 86.394±18.064* | 87.780±29.356* | 94.387±25.392* |

Table 2 Effects of PTH mimetic peptides in anti-bone loss through micro-CT observation (4 W, n=8)

|  | Sham | OVX | | | | |
|---|---|---|---|---|---|---|
|  |  | Vehicle | PTH(3-34) | MY-1 | PTH(1-34) | MY-3 |
| BV/TV | 0.144±0.011* | 0.089±0.014 | 0.092±0.027 | 0.129±0.027* | 0.122±0.021* | 0.147±0.014** |
| BMD | 118.655±11.277* | 78.890±14.457 | 80.890±11.321 | 101.597±20.486* | 103.645±19.559* | 119.509±10.359** |

PTH MIMETIC PEPTIDE BASED ON PROTEIN DOMAIN RECONSTRUCTION AND APPLICATION THEREOF

CROSS-REFERENCE TO RELATED APPLICATION

This application is a continuation-in-part of international application of PCT application serial no. PCT/CN2018/114335 filed on Nov. 7, 2018, which claims the priority benefit of China application no. 201811284147.2 filed on Oct. 31, 2018. The entirety of each of the above mentioned patent applications is hereby incorporated by reference herein and made a part of this specification.

BACKGROUND

Technical Field

The present disclosure belongs to biotechnology, in particular to a novel PTH mimetic peptide based on protein domain reconstruction and its applications.

Description of Related Art

Osteoporosis is a systemic skeletal disease characterized by low bone mass, degeneration of bone microstructure, increased bone fragility and susceptibility to fractures. It is a common disease severely affecting the health and life of elderly people. At present, the common treatments for osteoporosis include anti-bone resorption drugs and bone synthesis promoting drugs, in which the former is unable to effectively improve bone quality and need long-term medication, while the latter quickly improves bone quality and prevents fracture, especially for severe osteoporosis.

Parathyroid hormone (PTH) is a peptide hormone secreted by the parathyroid gland, and it is an important factor in regulating the balance of calcium and phosphorus metabolism in the body. Teriparatide (PTH (1-34)) is an amino-terminal polypeptide fragment of natural parathyroid hormone, and it is the only osteogenic drug widely prescribed on the market. A large number of clinical applications have proved its unique effectiveness. It can be used for severe osteoporosis and fracture healing. In general, teriparatide reduces the incidence of vertebral fractures by about 76%, but there is no definite conclusion about its preventive effect on hip fractures. Therefore, the development of better anti-osteoporosis drugs still has good prospects.

PTH (1-34) can promote both bone synthesis and bone resorption because it activates multiple signaling pathways. The net effect of PTH (1-34), when it is used intermittently at a small dose, is bone synthesis. When it is used continuously at a large dose, the net effect is bone resorption. How to improve the ability of bone synthesis, reduce or even block the ability of bone resorption is the general thinking of developing more effective anti-osteoporosis drugs. However, it was found in recent studies on sclerostin antibodies that if the bone resorption elements in bone metabolism are inhibited, the effect of promoting bone formation is not long-lasting, because bone synthesis and bone resorption are two complementary processes in bone metabolism.

Our prophase study found that the repeated position 29-34 peptide fragments of PTH can specifically activate the PLC-independent PKC signal transduction pathway to promote osteogenesis without promoting osteoclasts. Therefore, we designed a novel PTH mimetic peptide based on protein domain reconstruction to retain its original osteoclast promoting function and increase its osteogenic function, which has obtained good results in vitro and in vivo.

SUMMARY

The object of the present disclosure is to provide a novel PTH mimetic peptide based on protein domain reconstruction, which can promote osteoblast differentiation, has excellent outcomes in the treatment of osteoporosis, and has a significant clinical application prospect.

The technical solution to achieve the objective above is as follows:

A novel PTH (1-34) mimetic peptide based on protein domain reconstruction, wherein the mimetic peptide contained peptide fragment repeats at the 29-34th positions.

In one of the embodiments, the said peptide fragment at position 29-34 repeated once. The structure of the said mimetic peptide was: PTH (1-34) (29-34), and the amino acid sequence was: SEQ ID NO. 2.

In one of the embodiments, the said peptide fragment at position 29-34 repeated once, wherein the amino acid at position 34 and the last amino acid of the peptide fragment repeats at position 29-34 were changed from phenylalanine (Phe, F) into tyrosine (Tyr, Y), and the structure of the said mimetic peptide was: PTH(1-$^F$34$^Y$)(29-$^F$34$^Y$). The amino acid sequence was: SEQ ID NO. 3, which was referred to as MY-3 peptide.

In one of the embodiments, the said peptide fragment at positions 29-34 repeated once, wherein two amino acids were cut off from the mimetic peptide at the N-terminal. The amino acid at position 34 and the last amino acid of the peptide fragment repeats at positions 29-34 were changed from phenylalanine (Phe, F) into tyrosine (Tyr, Y), and the structure of the described mimetic peptide was: PTH(3-$^F$34$^Y$)(29-$^F$34$^Y$). The amino acid sequence was: SEQ ID NO. 5, which was referred to as MY-1 peptide.

Another object of the present disclosure is the use of the PTH mimetic peptide in the medicaments preparation for preventing or treating osteoporosis.

Another object of the present disclosure is to provide a medicine for preventing or treating osteoporosis or promoting bone growth, of which the active ingredient contains the PTH mimetic peptide.

A pharmaceutical composition for preventing or treating osteoporosis or promoting bone growth, including active ingredient and a pharmaceutically acceptable carrier, wherein the active ingredient contains any one of the said PTH mimetic peptide.

The beneficial effects of the present disclosure are:

1. Cell experiments proved that the MY-3 peptide of the present disclosure had better effects/result in promoting osteoblast differentiation than PTH (1-34), while the osteoclast promoting effect was not higher than PTH (1-34).

2. Animal experiments proved that MY-3 peptide had better osteoporosis prevention effect than PTH (1-34), showing that said PTH mimetic peptide had better clinical medicinal value for the treatment of osteoporosis.

BRIEF DESCRIPTION OF THE DRAWINGS

FIGS. 3A-3D show that in Example 3, MY-3 has a stronger effect on promoting osteogenic gene expression than PTH (1-34), and both have the same effect on promoting osteoclast differentiation gene expression.

DESCRIPTION OF THE EMBODIMENTS

A more comprehensive description about the present disclosure is as below.

The present disclosure provides a novel PTH mimetic peptide based on protein domain reconstruction, named PTH mimetic peptide (MY-3 peptide) with amino acid sequence SEQ ID No.3. MY-3 peptide is modified based on SEQ ID NO.1, the natural PTH (1-34). Firstly, the 29-34 peptide fragment is repeated once, and then the amino acid at the 34th position and the last amino acid of the repeated peptide fragment at position 29-34 are changed from phenylalanine (Phe, F) into tyrosine (Tyr, Y). After the modification, the ability of MY-3 peptide to promote bone synthesis is enhanced.

TABLE 1

Amino acid sequence of PTH mimetic peptide.

| SEQ ID NO | Sequence composition | Amino acid sequence (Indicated by the abbreviation of amino acid) | Code name |
|---|---|---|---|
| SEQ ID NO. 1 | PTH (1-34) | SVSEIQLMHNLGKHLNSMERV EWLRKKLQDVHNF | PTH (Parathyroid hormone) |
| SEQ ID NO. 2 | PTH(1-34) (29-34) | SVSEIQLMHNLGKHLNSMERV EWLRKKLQDVHNFQDVHNF | |
| SEQ ID NO. 3 | PTH(1-$F34^Y$) (29-$F34^Y$) | SVSEIQLMHNLGKHLNSMERV EWLRKKLQDVHNYQDVHNY | MY-3 |
| SEQ ID NO. 4 | PTH (3-$F34^Y$) | SEIQLMHNLGKHLNSMERVEW LRKKLQDVHNY | |
| SEQ ID NO. 5 | PTH(3-$F34^Y$) (29-$F34^Y$) | SEIQLMHNLGKHLNSMERVEW LRKKLQDVHNYQDVHNY | MY-1 |

Example 1

MY-3 has stronger osteoblast differentiation effect than PTH (1-34) during intermittent stimulation; both have the same osteoclast differentiation effect.

Osteoblasts were isolated from the skulls of newborn mice and cultured in vitro. The cell at density of $1\times10^5$/well was inoculated in a 24-well culture plate. After 3 days, a 4 h/48 h intermittent PTH mimetic peptide stimulation experiment was started, which the PTH mimetic peptide was added to the culture system at the corresponding concentration (containing 10% serum+α-MEM Culture medium). After 4 hours, the culture solution was aspirated, the adherent cells were gently washed once with α-MEM medium, then 10% serum+α-MEM medium was added and continued culturing for 44 hours. Repeated this cycle. Concentration: MY-1 peptide $10^{-6}$ M, PTH (1-34) peptide $10^{-8}$M, MY-3 peptide $10^{-8}$ M.

Figure 1A:
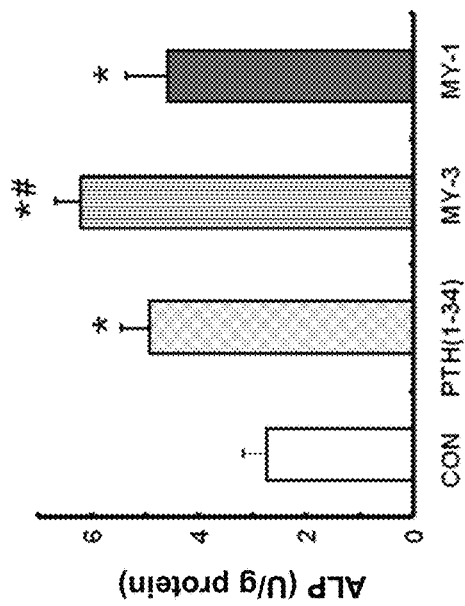
FIGS. 1A-1D show that in Example 1, MY-3 has stronger osteoblast differentiation effect than PTH (1-34) during intermittent stimulation, and both have the same osteoclast differentiation effect.
Figure 1B:
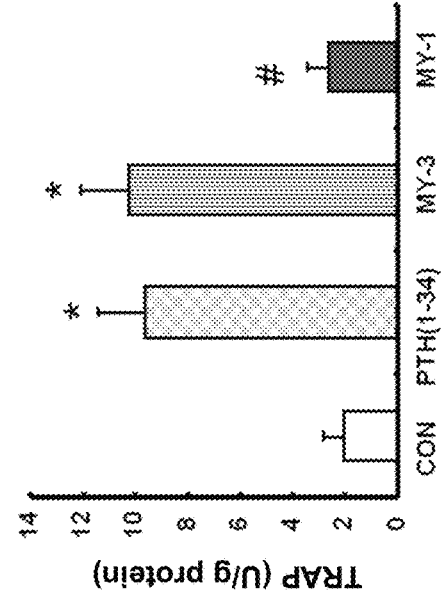
Figure 1C:
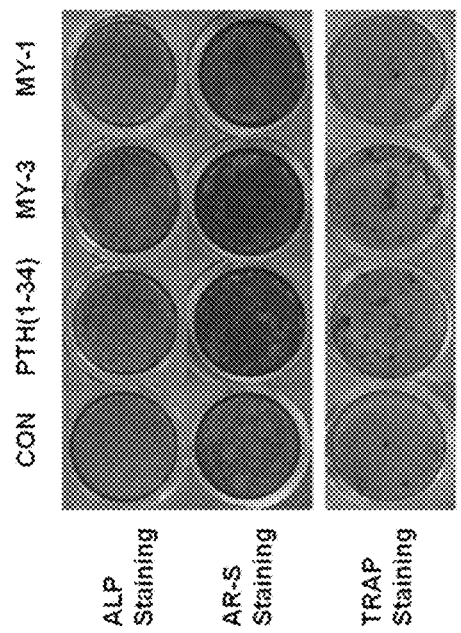

Alkaline phosphatase staining was performed after 2 weeks, and calcium nodule staining was performed after 4 weeks (FIG. 1A, upper two rows of the holes). Alkaline phosphatase expression and calcium ion concentration of each well were quantitative detected (FIGS. 1B and 1C). It was found that PTH (1-34), MY-1 peptide and MY-3 peptide can promote osteogenic differentiation of osteoblasts, and MY-3 is significantly stronger than PTH (1-34).

Figure 1D:
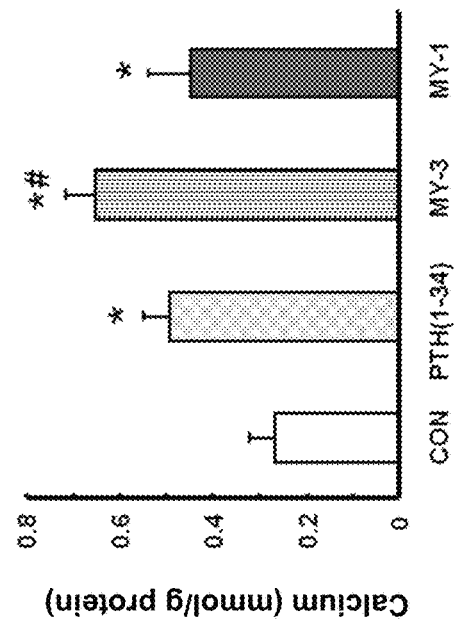

Bone marrow cells from the bone marrow cavity of 7-week-old mice were extracted and cultured in 24-well plates at a density of $1\times10^5$/well. The 4 h/48 h intermittent PTH mimetic peptide stimulation experiment was carried out as described above. After 7 days, tartrate resistant acid phosphatase (TRAP) staining (bottom row of the holes in FIG. 1A) and quantification were performed (FIG. 1D). It was shown that MY-1 peptide did not promote the osteoclasts formation, while MY-3 peptide and PTH (1-34) had the same effect of promoting osteoclast formation.

TABLE 2 data involved in FIGs. 1B, 1C and 1D

| | Control | PTH (1-34) | MY-3 | MY-1 |
|---|---|---|---|---|
| ALP (U/g protein) | 2.72 ± 0.43 | 4.91 ± 0.55 | 6.19 ± 0.47 | 4.57 ± 0.79 |
| Calcium (mmole/g protein) | 0.27 ± 0.06 | 0.49 ± .06 | 0.65 ± 0.07 | 0.45 ± 0.09 |
| TRAP (U/g protein) | 2.05 ± 0.79 | 9.61 ± 1.78 | 10.26 ± 1.82 | 2.64 ± 0.81 |

The results of Example 1 are shown in FIG. 1. Primary osteoblasts (two rows of the holes in A) of mouse skulls were intermittently treated with PTH (1-34), MY-3 and MY-1. (within 48 hours, PTH peptide was added to the medium for 4 hours, removed, and cultured in the ordinary medium for 44 hours, then started all over again). At 2 weeks, alkaline phosphatase (ALP) staining (A) and quantification (B) wells were performed in the cell culture. 4 Weekly, calcium nodule staining (A) and calcium ion quantification (C) were performed in culture wells. Bone marrow cells in the femoral shaft bone marrow cavity (lower hole A) received the same treatment with three peptides mentioned above. Two weeks later, tartrate resistant acid phosphatase (TRAP) staining (A) and quantification (D) were performed. The histogram shows the average and standard deviation of an independent experiment (triple-well). The same experiment was repeated three times, and same results were obtained. *$P<0.05$ vs control group (CON), #$P<0.05$ vs PTH (1-34).

Example 2

MY-3 has a weaker effect on inhibiting osteoblast differentiation than PTH (1-34) during continuous stimulation, and both have the same osteoclast differentiation promoting effect.

Figure 2A:
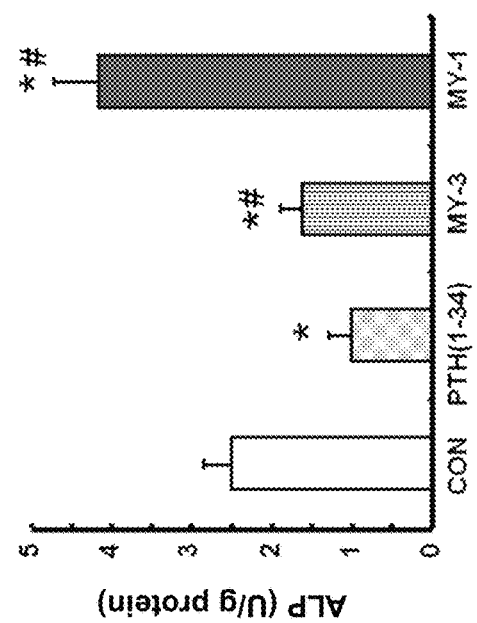
FIGS. 2A-2D show that in Example 2, MY-3 has a weaker effect on inhibiting osteoblast differentiation than PTH (1-34) during continuous stimulation, and both have the same osteoclast differentiation promoting effect.
Figure 2B:
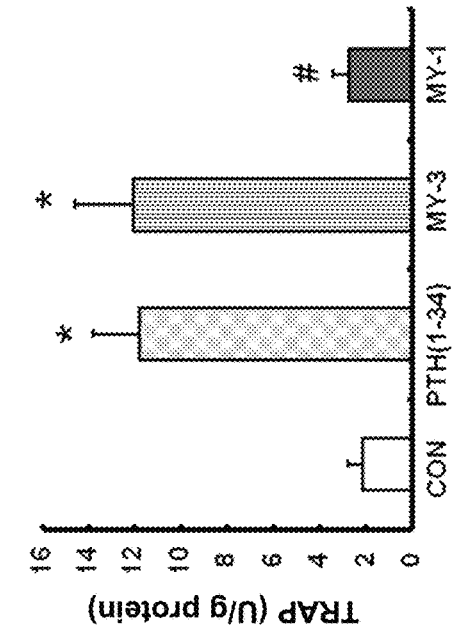
Figure 2C:
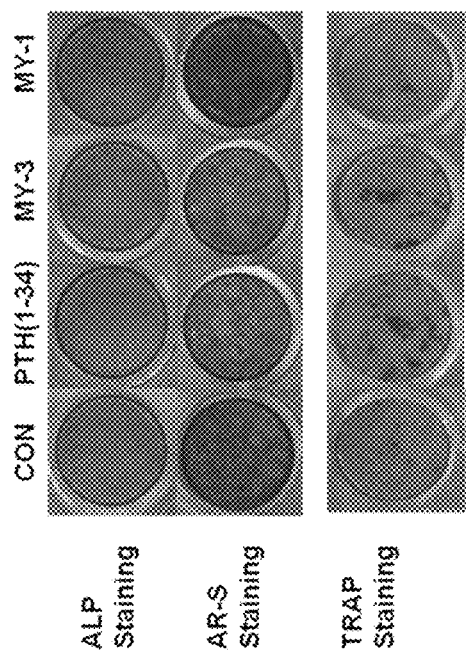

Osteoblasts were isolated from the skulls of newborn mice and cultured in vitro. The cell at density of $1\times10^5$/well was inoculated in the 24-well culture plate. After 3 days, the continuous PTH mimetic peptide stimulation experiment was started. The PTH mimetic peptide was added to the culture system (containing 10% serum+α-MEM medium) at the corresponding concentration. After 48 hours, when the medium is changed, the PTH mimetic peptide was added again, meaning the PTH mimetic peptide is always in the culture solution. Concentration: MY-1 peptide $10^{-6}$M, PTH (1-34) peptide $10^{-8}$ M, MY-3 peptide $10^{-8}$ M. Alkaline phosphatase staining was performed 2 weeks later, and calcium nodule staining was performed 4 weeks later (FIG. 2A, upper two rows of the holes). The expression of alkaline phosphatase and the concentration of calcium ion in each well were quantitatively detected (FIGS. 2B and 2C). It was found that PTH (1-34) and MY-1 peptides promote the osteogenic differentiation of osteoblasts, while MY-3 and PTH (1-34) inhibit the differentiation of osteoblasts, and the inhibitory effect of MY-3 peptides is weak.

Figure 2D:
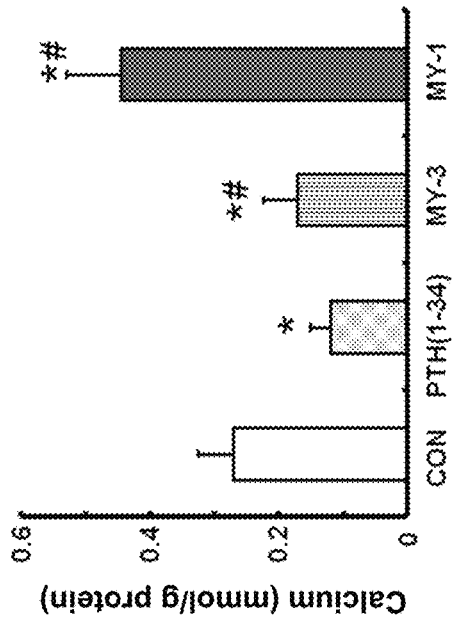

Bone marrow cells from the bone marrow cavity of femur in 7-week-old mice were extracted and seeded in 24-well plates at a density of $1\times10^5$/well. The 48 h continuous PTH mimetic peptide stimulation experiment was carried out as described above. After 7 days, tartrate resistant acid phosphatase (TRAP) staining (bottom row of holes in FIG. 2A) and quantification were performed (FIG. 2D). It was shown that MY-1 peptide does not promote the production of osteoclasts, while MY-3 peptide and PTH (1-34) have the same effect on promoting osteoclast formation.

TABLE 3 data involved in FIGs. 2B, 2C and 2D

| | Control | PTH (1-34) | MY-3 | MY-1 |
|---|---|---|---|---|
| ALP (U/g protein) | 2.51 ± 0.34 | 1.02 ± 0.28 | 1.62 ± 0.28 | 4.15 ± 0.56 |
| Calcium (mmole/g protein) | 0.27 ± 0.05 | 0.12 ± 0.03 | 0.17 ± 0.05 | 0.44 ± 0.08 |
| TRAP (U/g protein) | 2.14 ± 0.64 | 11.80 ± 1.99 | 12.07 ± 2.53 | 2.76 ± 0.69 |

The results of Example 2 are shown in FIG. 2. Primary osteoblasts (two rows of the holes in A) of mouse skulls were continuously treated with PTH (1-34), MY-3 and MY-1 (within the 48-hour culture cycles, PTH peptide stayed in the culture medium at all times). After 2 weeks, alkaline phosphatase (ALP) staining (A) and quantification (B) wells were performed in the cell culture. After 4 Weeks, calcium nodule staining (A) and calcium ion quantification (C) were performed in culture wells. Bone marrow cells in the femoral shaft bone marrow cavity (lower hole A) received the same treatment with three peptides as described above. Two weeks later, tartrate resistant acid phosphatase (TRAP) staining (A) and quantification (D) were performed. The histogram shows the average and standard deviation of an independent experiment (triple wells). The same experiment was repeated three times and same results were obtained. *$P<0.05$ vs control group (CON), #$P<0.05$ vs PTH (1-34).

Example 3

MY-3 has a stronger effect of promoting osteogenic gene expression than PTH (1-34), and both have the same effect of promoting expressing of the osteoclast differentiation genes.

Primary mouse skull osteoblasts (FIGS. 3A and 3B) and mouse bone marrow cells (FIGS. 3C and 3D) were cultured in cell culture plates. When the cells completely cover the bottom of the culture well, changed to a medium containing 1% fetal bovine serum, added with different concentrations of PTH mimetic peptide (the concentration is the same as above). Cells receiving intermittent stimulation (FIG. 3A and FIG. 3C) were treated with PTH peptides for 4 hours, and normal medium for 44 hours. Such 48-hour cycle repeated three times.

Cell RNA was extracted 4 hours after the last PTH peptide stimulation for Realtime PCR detection. Cells receiving continuous stimulation (FIG. 3B and FIG. 3D) were cultured in the medium with PTH peptides, and the culture medium containing peptides was changed 48 hours later. Repeated such cycle three times. After 48 hours of the last PTH peptide stimulation, cellular RNA was extracted for Real-time PCR detection. As shown in the figure, the average value and standard deviation of an independent experiment (triple holes) were obtained. The same experiment was repeated three times and same results were obtained. *$P<0.05$ vs control group (CON), #$P<0.05$ vs PTH (1-34).

Intermittent stimulation with PTH (1-34), MY-1 peptide, and MY-3 peptide can all promote the expression of osteogenic marker gene ALP and OC, and the stimulation effect of MY-3 on ALP and OC genes is stronger than that of PTH (1-34). The stimulation effect of My-3 on osteoclast gene RANKL was weaker than that of PTH (1-34) (FIG. 3C). After continuous stimulation of bone marrow cells (FIG. 3D), both MY-3 and PTH (1-34) inhibited the expression of ALP and OC. Both significantly promoted RANKL expression.

Example 4

MY-3 has stronger anti-bone loss effect than PTH (1-34), through microscopic CT observation.

Figure 4:
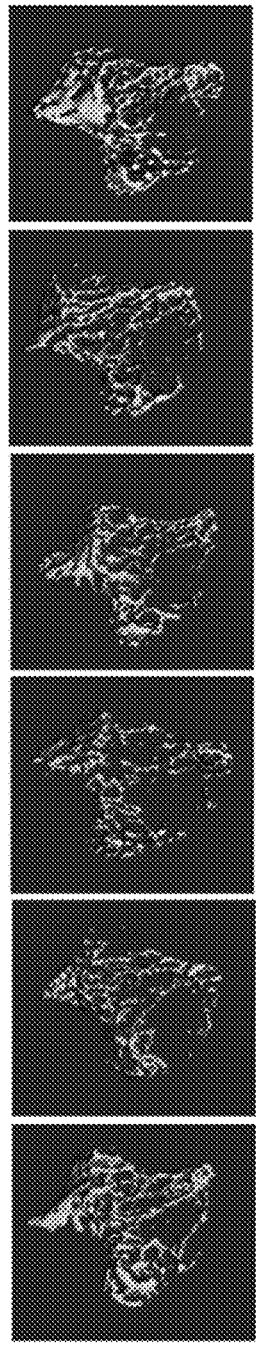
FIG. 4 shows that in Example 4, MY-3 has a stronger anti-bone loss effect than PTH (1-34), through microscopic CT observation.
Figure 4:
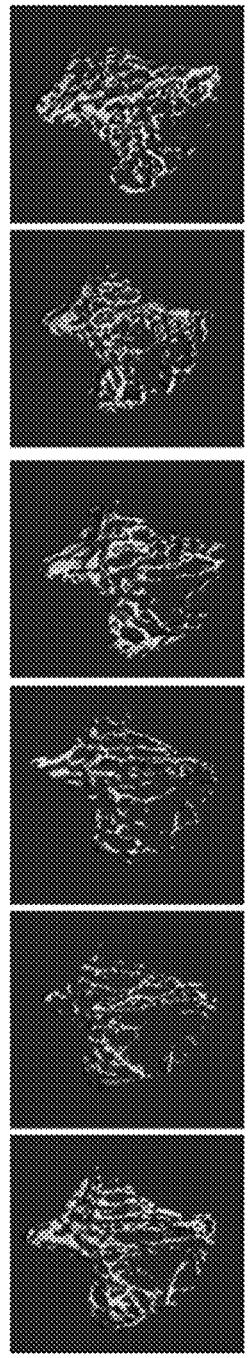

An osteoporosis model was constructed by removing the ovaries of 7-week-old C57BL female mice. Mice were subcutaneously injected with PTH (3-34) (400 µg/kg/day), MY-1 peptide (400 µg/kg/day), PTH (1-34) (40 µg/kg/day) and MY-3 peptide (40 µg/kg/day) daily (5 days a week), respectively. Mice were sacrificed at 2 and 4 weeks and their tibias were separated, then the cancellous bone mass (BV/TV) and bone mineral density (BMD) of the tibias were measured by micro-CT (FIG. 4). The table shows the average value and standard error of bone mass (BV/TV) and BMD of 8 mice, *$P<0.05$ vs control group (CON), #$P<0.05$ vs PTH (1-34). The image shows the three-dimensional reconstruction image of the cancellous bone of the upper tibia by micro-CT.

As a result, the My-3 peptide group has higher bone mass (BV/TV) and bone density (BMD) than that of PTH (1-34), so MY-3 has a significant enhancement in preventing bone loss caused by castration.

Example 5

MY-3 has a stronger anti-bone loss effect than PTH (1-34)-through histological studies.

Figure 5:
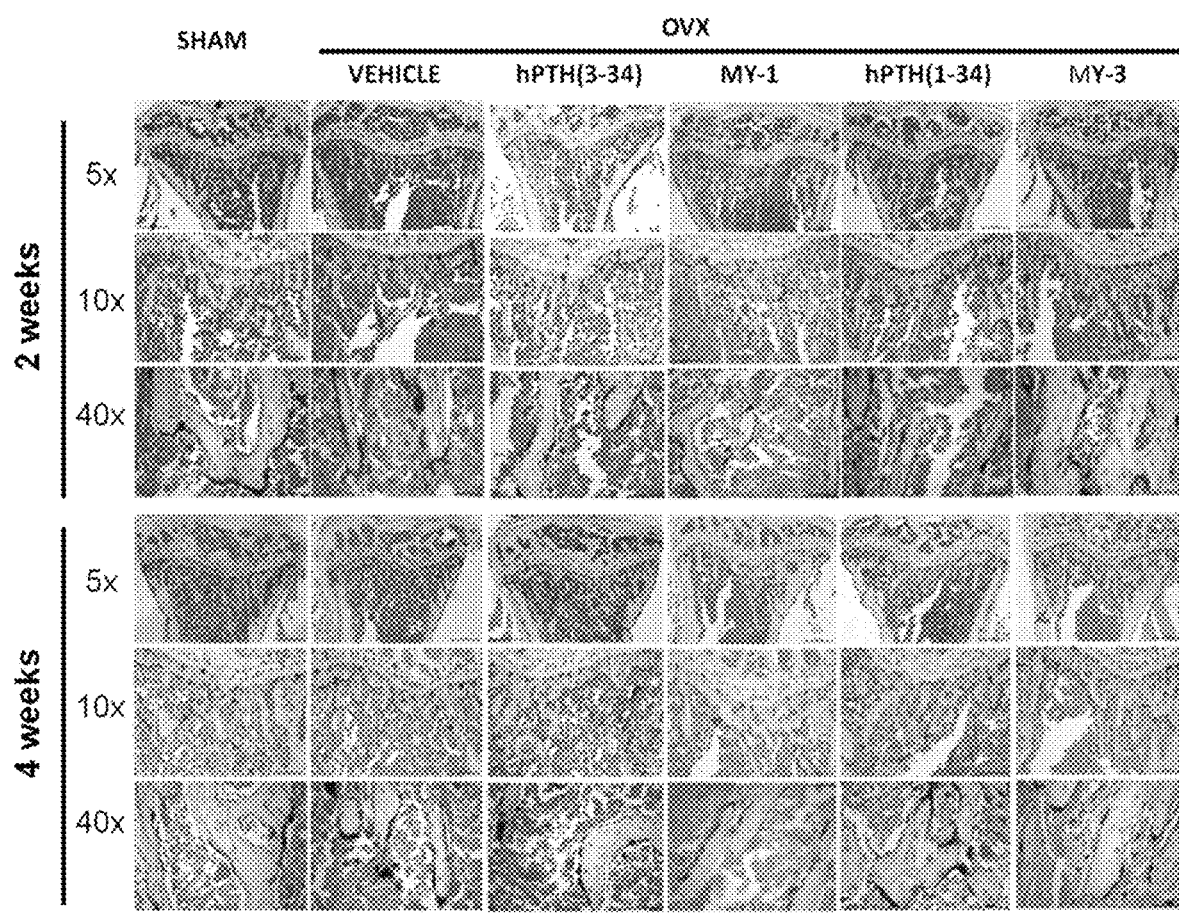
FIG. 5 shows that in Example 5, MY-3 has a stronger anti-bone loss effect than PTH (1-34)-through histological studies.

The preparation of the osteoporosis animal model and the administration method of the PTH mimetic peptide was the same as in Example 4. After 2 and 4 weeks, the tibias of experimental mice were removed, decalcified, and prepared for paraffin section. At last, the osteoclast was stained. As shown in FIG. 5, no matter whether it is 2 weeks or 4 weeks, after ovariectomy (OVX), the number of trabecular bones were significantly reduced, but when compared with the control group, it is increased after treated with PTH (1-34), MY-1 and MY-3 peptide. The effect of MY-3 peptide was significantly higher than that of PTH (1-34), which was consistent with the results of micro-CT.

The results suggest that MY-3 might be an effective anti-osteoporosis drug in the future. Moreover, MY-3 has strong bone-promoting function. Animal experiments have proved that MY-3 has a significant effect compared to PTH (1-34) and may become the strongest anti-osteoporosis drug.

The above examples are only specific embodiments of the invention and do not limit the protection scope of the invention accordingly. Any substitution or improvement made without violating the conception of the present disclosure should be considered as the scope of the specification herein.

What is claimed is:

1. A PTH(1-34) mimetic peptide, wherein the mimetic peptide contains peptide fragment repeats at 29th-34th positions, wherein structure of the mimetic peptide is PTH(1-34)(29-34), and the amino acid sequence of the mimetic peptide is SEQ ID NO: 2.

2. A pharmaceutical composition for preventing or treating osteoporosis or promoting bone growth, comprising an active ingredient and a pharmaceutically acceptable carrier, wherein the active ingredient of the pharmaceutical composition contains the PTH mimetic peptide according to claim 1.

* * * * *

```
                          SEQUENCE LISTING

<160> NUMBER OF SEQ ID NOS: 5

<210> SEQ ID NO 1
<211> LENGTH: 34
<212> TYPE: PRT
<213> ORGANISM: Artificial Sequence
<220> FEATURE:
<223> OTHER INFORMATION: Synthesized polypeptide

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 40
<212> TYPE: PRT
<213> ORGANISM: Artificial Sequence
<220> FEATURE:
<223> OTHER INFORMATION: Synthesized polypeptide

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Gln Asp Val His Asn Phe
            35                  40

<210> SEQ ID NO 3
<211> LENGTH: 40
<212> TYPE: PRT
<213> ORGANISM: Artificial Sequence
<220> FEATURE:
<223> OTHER INFORMATION: Synthesized polypeptide

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Tyr Gln Asp Val His Asn Tyr
            35                  40

<210> SEQ ID NO 4
<211> LENGTH: 32
<212> TYPE: PRT
<213> ORGANISM: Artificial Sequence
<220> FEATURE:
<223> OTHER INFORMATION: Synthesized polypeptide

<400> SEQUENCE: 4

Ser Glu Ile Gln Leu Met His Asn Leu Gly Lys His Leu Asn Ser Met
1               5                   10                  15

Glu Arg Val Glu Trp Leu Arg Lys Lys Leu Gln Asp Val His Asn Tyr
            20                  25                  30
```

```
-continued

<210> SEQ ID NO 5
<211> LENGTH: 38
<212> TYPE: PRT
<213> ORGANISM: Artificial Sequence
<220> FEATURE:
<223> OTHER INFORMATION: Synthesized polypeptide

<400> SEQUENCE: 5

Ser Glu Ile Gln Leu Met His Asn Leu Gly Lys His Leu Asn Ser Met
1               5                   10                  15

Glu Arg Val Glu Trp Leu Arg Lys Lys Leu Gln Asp Val His Asn Tyr
            20                  25                  30

Gln Asp Val His Asn Tyr
        35
```